United States Patent
Starling et al.

(10) Patent No.: US 9,969,971 B2
(45) Date of Patent: May 15, 2018

(54) CALCIUM-CONTAINING STRUCTURES AND METHODS OF MAKING AND USING THE SAME

(71) Applicant: CAP BIOTECHNOLOGY INC, Golden, CO (US)

(72) Inventors: L. Brian Starling, Golden, CO (US); James E. Stephan, Arvada, CO (US)

(73) Assignee: CAP Biotechnology, Inc., Golden, CO (US)

( * ) Notice: Subject to any disclaimer, the term of this patent is extended or adjusted under 35 U.S.C. 154(b) by 0 days. days.

(21) Appl. No.: 13/784,398

(22) Filed: Mar. 4, 2013

(65) Prior Publication Data

US 2013/0243737 A1    Sep. 19, 2013

Related U.S. Application Data

(63) Continuation of application No. 10/030,578, filed as application No. PCT/US00/18712 on Jul. 7, 2000, now Pat. No. 8,389,017.

(60) Provisional application No. 60/143,333, filed on Jul. 8, 1999.

(51) Int. Cl.
| | |
|---|---|
| *C12N 5/00* | (2006.01) |
| *A61K 9/50* | (2006.01) |
| *A61K 33/06* | (2006.01) |
| *A61K 45/06* | (2006.01) |
| *A61L 27/12* | (2006.01) |
| *A61L 27/36* | (2006.01) |
| *A61L 27/50* | (2006.01) |
| *A61L 27/54* | (2006.01) |
| *C12N 5/077* | (2010.01) |
| *A61K 35/12* | (2015.01) |

(52) U.S. Cl.
CPC ........... *C12N 5/0075* (2013.01); *A61K 9/501* (2013.01); *A61K 33/06* (2013.01); *A61K 45/06* (2013.01); *A61L 27/12* (2013.01); *A61L 27/3608* (2013.01); *A61L 27/50* (2013.01); *A61L 27/54* (2013.01); *C12N 5/0654* (2013.01); *A61K 35/12* (2013.01); *A61L 2300/114* (2013.01); *C12N 2533/18* (2013.01)

(58) Field of Classification Search
CPC ........ A61K 8/0279; A61K 8/19; A61K 9/501; C12N 5/0075
USPC ........ 424/400, 489, 490, 491, 497, 602, 680
See application file for complete search history.

(56) References Cited

U.S. PATENT DOCUMENTS

| | | | |
|---|---|---|---|
| 3,875,273 A | 4/1975 | Martin | |
| 4,217,370 A | 8/1980 | Rawlings et al. | |
| 4,257,798 A | 3/1981 | Hendricks et al. | |
| 4,448,884 A | 5/1984 | Henderson | |
| 4,472,840 A | 9/1984 | Jefferies | |
| 4,547,233 A | 10/1985 | Delzant et al. | |
| 4,564,532 A | 1/1986 | Henderson | |
| 4,661,407 A | 4/1987 | Henderson | |
| 4,678,470 A | 7/1987 | Nashef et al. | |
| 4,757,017 A * | 7/1988 | Cheung | 435/384 |
| 4,777,153 A * | 10/1988 | Sonuparlak | B32B 18/00 |
| | | | 264/44 |
| 4,777,154 A | 10/1988 | Torobin | |
| 4,798,585 A | 1/1989 | Inoue et al. | |
| 4,916,173 A * | 4/1990 | Otloski | C08G 18/0885 |
| | | | 521/54 |
| 4,987,068 A | 1/1991 | Trosch et al. | |
| 5,011,495 A | 4/1991 | Hollinger | |
| 5,045,201 A | 9/1991 | Dubois et al. | |
| 5,047,031 A | 9/1991 | Constantz | |
| 5,085,861 A | 2/1992 | Gerhart et al. | |
| 5,171,326 A | 12/1992 | Ducheyne et al. | |
| 5,192,324 A | 3/1993 | Kenna | |
| 5,225,123 A | 7/1993 | Torobin | |
| 5,262,320 A | 11/1993 | Stephanopoulos et al. | |
| 5,273,964 A | 12/1993 | Lemons | |
| 5,324,519 A | 6/1994 | Dunn et al. | |

(Continued)

FOREIGN PATENT DOCUMENTS

| | | |
|---|---|---|
| CA | 2129993 | 8/1993 |
| CA | 2128783 | 9/1993 |

(Continued)

OTHER PUBLICATIONS

International Search Report for International (PCT) Patent Application No. PCT/US00/18712, dated Sep. 22, 2000.

(Continued)

*Primary Examiner* — Ruth A Davis

(74) *Attorney, Agent, or Firm* — Sheridan Ross P.C.

(57) ABSTRACT

The present invention generally relates to calcium-containing structures and methods of making and using the structures. In one aspect, hollow calcium containing microstructures are used in conjunction with bone tissues/by-products to augment bone defects and extend the supply of bone tissues/by-products for bone augmentation. Bonding agents, such as calcium cements, are also used in the preparation of the hollow calcium microstructures combined with bone tissues/by-products or for use in preparing the hollow microstructures. The calcium-containing microstructures of the present invention are also useful as delivery vehicles of nitric oxide and/or nitric oxide containing or producing compounds for a variety of in vitro and in vivo uses. Calcium containing contoured substrates upon which cells/tissues can be grown in vitro for replacement and repair of tissues in vivo that conform in size and shape to the tissue surface to be replaced are also provided.

6 Claims, No Drawings

(56) References Cited

U.S. PATENT DOCUMENTS

| | | | |
|---|---|---|---|
| 5,397,759 A | 3/1995 | Torobin | |
| 5,405,919 A | 4/1995 | Keefer et al. | |
| 5,422,340 A | 6/1995 | Ammann et al. | |
| 5,480,827 A | 1/1996 | Guillemin et al. | |
| 5,492,822 A | 2/1996 | Lange, III et al. | |
| 5,496,722 A * | 3/1996 | Goodwin et al. | 435/371 |
| 5,510,262 A | 4/1996 | Stephanopoulos et al. | |
| 5,525,148 A | 6/1996 | Chow et al. | |
| 5,538,887 A | 7/1996 | Peindhl et al. | |
| 5,716,413 A | 2/1998 | Walter et al. | |
| 5,741,215 A * | 4/1998 | D'Urso | A61F 2/30942 128/898 |
| 5,797,887 A | 8/1998 | Rosen et al. | |
| 5,803,963 A | 9/1998 | Dry | |
| 5,814,666 A | 9/1998 | Green et al. | |
| 5,897,556 A | 4/1999 | Drewry et al. | |
| 5,922,025 A | 7/1999 | Hubbard | |
| 5,948,516 A * | 9/1999 | Kriven et al. | 428/216 |
| 5,965,264 A | 10/1999 | Barenberg et al. | |
| 5,994,444 A | 11/1999 | Trescony et al. | |
| 6,210,715 B1 | 4/2001 | Starling et al. | |
| 6,358,531 B1 | 3/2002 | Day et al. | |
| 6,358,532 B2 | 3/2002 | Starling et al. | |
| 6,416,774 B1 | 7/2002 | Radin et al. | |
| 8,389,017 B1 | 3/2013 | Starling et al. | |

FOREIGN PATENT DOCUMENTS

| | | |
|---|---|---|
| CA | 2253649 | 11/1997 |
| EP | 0271236 | 6/1988 |
| EP | 0413492 | 2/1991 |
| EP | 0719529 | 7/1996 |
| WO | WO 86/02093 | 4/1986 |
| WO | WO 96/05038 | 2/1996 |
| WO | WO 97/40137 | 10/1997 |
| WO | WO 97/41842 | 11/1997 |
| WO | WO 97/45147 | 12/1997 |
| WO | WO 98/43558 | * 10/1998 |
| WO | WO 00/46147 | 8/2000 |

OTHER PUBLICATIONS

International Preliminary Examination Report for International (PCT) Patent Application No. PCT/US00/18712, dated Aug. 3, 2001.

Notice of Allowance for Canadian Application No. 2,377,747, dated Jan. 15, 2009.

Official Action for Canadian Application No. 2,377,747, dated Oct. 16, 2007.

Official Action for Canadian Application No. 2,377,747, dated May 4, 2006.

Official Action for Canada Patent Application No. 2,669,457, dated Jun. 16, 2011 2 pages.

Notice of Allowance for Canada Patent Application No. 2,669,457, dated Feb. 2, 2012, 1 page.

Decision to Grant for European Application No. 00947146.7, dated Oct. 20, 2008.

Official Action for European Application No. 00947146.7, dated May 8, 2008.

Official Action for European Application No. 00947146.7, dated Nov. 24, 2006.

Official Action for European Application No. 00947146.7, dated Jul. 12, 2006.

Official Action for European Application No. 00947146.7, dated Sep. 29, 2005.

Supplementary European Search Report issued by the European Patent Office for Application No. EP 00947146.7, dated Jun. 22, 2005.

Supplementary Partial European Search Report issued by the European Patent Office for Application No. EP 00947146.7, dated Apr. 6, 2005.

Extended European Search Report for European Patent Application No. 091573386, dated May 28, 2009, 10 pages.

Official Action for European Patent Application No. 09157338.6, dated Jun. 11, 2012, 10 pages.

Official Action issued by the European Patent Office for Application No. 09157338.6, dated Jan. 29, 2010.

Extended Search Report for European Patent Application No. 10178704.2, dated Dec. 3, 2010.

Official Action for European Patent Application No. 10178704.2, dated Jun. 11, 2012.

"Bio-Gel® HPHT for Protein and Nucleic Acid HPLC: New High Performance Hydroxylapatite Column—Bulletin No. 1115," Bio-Rad Laboratories, 1986, 4 pages.

Aoki, *Medical Applications of Hydroxyapatite*, Ishiyaku EuroAmerica, Inc. 1994, (contents), 6 pages.

Arita et al. "Synthesis and processing of hydroxyapatite ceramic tapes with controlled porosity," Journal of Materials Science. Materials in Medicine, 1995, vol. 6, No. 1, pp. 19-23.

Cartwright et al., "Culture media," *Basic Cell Culture: A Practical Approach*, Oxford University Press, New York, 1994, pp. 74-81.

Ea et al. "Octacalcium phosphate crystals directly stimulate expression of inducible nitric oxide synthase through p38 and JNK mitogen-activated protein kinases in articular chondrocytes," Arthritis Research and Therapy, 2005, vol. 7, No. 5, pp. R915-926.

El Deeb, et al., "Osteogenesis in Composite Grafts of Allergenic Demineralized Bone Powder and Porous Hydroxylapatite", The Journal of Oral and Maxilofacial Surgery, 1989, vol. 47, pp. 50-56.

Gepstein et al., "Bridging large defects in bone by demineralized bone matrix in the form of a powder. A radiographic, histological, and radioisotope-uptake study in rats.," Journal of Bone and Joint Surgery,1987, vol. 69, No. 7, pp. 984-992.

Jordan et al. "Regulation of inducible nitric oxide production by intracellular calcium," Surgery, 1995, vol. 118, No. 2, pp. 138-146.

Klosterman et al. "Interfacial characteristics of composites fabricated by laminated object manufacturing," Composites Part A: Applied Science and Manufacturing, 1998, vol. 29, No. 9-10, pp. 1165-1174.

Krajewski et al. "The processing of hydroxyapatite-based rolled sections," Biomaterials, 1982, vol. 3, Iss. 2, pp. 117-120.

Lee et al., "High Intensity Growth of Adherent Cells on a Porous Ceramic Matrix," *Production of Biologicals from Animal Cells in Culture*, Butterworth-Heinemann Ltd, Oxford, 1991, pp. 400-405.

Looby et al., "Immobilization of animal cells in porous carrier culture," Trends in Biotechnology, 1990, vol. 8, No. 8, pp. 204-209.

Matsushita et al., "High density culture of anchorage-dependent animal cells by polyurethane foam packed-bed culture systems," Applied Microbiology and Biotechnology, 1991, vol. 35, Iss. 2, pp. 159-164.

Ohyama et al., β-Tricalcium Phosphate Combined with Recombinant Human Bone Morphogenetic Protein-2: A Substitute for Autograft, Used for Packing Interbody Fusion Cages in the Canine Lumbar Spine, Neurologia Medico-Chirurfica (Tokyo), 2004, vol. 44, pp. 234-241.

Park et al., "Packed Bed Bioreactor with Porous Ceramic Beads for Animal Cell Culture," Biotechnology and Bioengineering, 1993, vol. 41, pp. 25-34.

Pelsue, et al., "Bone Induction by Hydroxapatite beads with cancellous bone and bone matrix: A preliminary study in the rat", Manuscript from the Comparative Oncology Unit, Departments of Clinical Sciences, and Pathology, College of Veterinary Medicine and Biomedical Sciences, Colorado State University, no date, 17 pages.

Pulfer, et al., "Incorporation of nitric oxide-releasing crosslinked polyethyleneimine microspheres into vascular grafts", Journal of Biomedical Materials Research, 1997, vol. 37, No. 2, pp. 182-189.

Qui et al., "Fabrication, characterization and evaluation of bioceramic hollow microspheres used as microcarriers for 3-D bone tissue formation in bioreactors," Biomaterials, vol. 20, 1999, pp. 989-1001.

Ripamonti, et al., "Tissue Engineering of Bone by Osteoinductive Biomaterials", MRS Bulletin, Nov. 1996, pp. 36-39.

Schmidt et al. "Ca2+/calmodulin-regulated nitric oxide synthases," Cell Calcium, 1992, vol. 13, No. 6-7, pp. 427-434.

(56) References Cited

OTHER PUBLICATIONS

Small, et al., "Augmenting the Maxillary Sinus for Implants: Report of 27 Patients," The International Journal of Oral & Maxillofacial Implants, 1993, vol. 8, No. 5, pp. 523-528.

Sundaram et al., "Liquid Chromatographic Assay for the Separation of Single- and Double-Stranded DNA by Using UV and UV Diode-Array Detectors and Hydroxylapatite Column," Journal of Liquid Chromatography, 1995, vol. 18, Iss. 5, pp. 925-939.

Tampieri et al., "Sintering and characterization of HA and TCP bioceramics with control of their strength and phase purity," Journal of Materials Science: Materials in Medicine, 1997, vol. 8, Iss. 1, pp. 29-37.

Wernike et al., "VEGF Incorporated into Calcium Phosphate Ceramics Promotes Vascularisation and Bone Formation In Vivo," European Cells and Materials, 2010, vol. 19, pp. 30-40.

Wilcox et al., eds., Hollow and Solid Spheres and Microspheres: Science and Technology Associated With Their Fabrication and Application: Materials Research Society Symposium Proceedings vol. 372, Materials Research Society, Pittsburgh, PA, 1995, (contents), 5 pages.

Woo et al., "Suppression of apoptosis by enhanced protein adsorption on polymer/hydroxyapatite composite scaffolds," Biomaterials, Jun. 2007, vol. 28(16), pp. 2622-2630.

Notice of Allowance for U.S. Appl. No. 10/030,578, dated Oct. 31, 2012, 5 pages.

Office Action for U.S. Appl. No. 10/030,578, dated Oct. 25, 2012, 5 pages.

Office Action for U.S. Appl. No. 10/030,578, dated Jun 7, 2011, 12 pages.

Office Action for U.S. Appl. No. 10/030,578, dated Apr. 27, 2010.

Office Action for U.S. Appl. No. 10/030,578, dated Aug. 31, 2009.

Office Action for U.S. Appl. No. 10/030,578, dated Jan. 22, 2009.

Office Action for U.S. Appl. No. 10/030,578, dated Oct. 26, 2007.

Office Action for U.S. Appl. No. 10/030,578, dated May 8, 2006.

Office Action for U.S. Appl. No. 10/030,578, dated Oct. 18, 2005.

Office Action for U.S. Appl. No. 10/030,578, dated Dec. 14, 2004.

Office Action for U.S. Appl. No. 10/030,578, dated Mar. 31, 2005.

Intention to Grant for European Patent Application No. 09157338.6, dated Feb. 16, 2015 20 pages.

\* cited by examiner

CALCIUM-CONTAINING STRUCTURES AND METHODS OF MAKING AND USING THE SAME

CROSS REFERENCE TO RELATED APPLICATIONS

The present application is a continuation application of U.S. application Ser. No. 10/030,578, filed Apr. 29, 2002, now U.S. Pat. No. 8,389,017, which is a national phase filing under 35 U.S.C. § 371 of PCT Application Serial No. PCT/US00/18712, filed Jul. 7, 2000, and which claims priority under 35 U.S.C. § 119(e) from U.S. Provisional Patent Application Ser. No. 60/143,333, filed Jul. 8, 1999.

FIELD OF THE INVENTION

The invention generally relates to calcium-containing structures for use as implantable substrates, cell culture substrates, carriers of nitric oxide and a variety of other uses.

BACKGROUND OF THE INVENTION

Revolutionary advances in biotechnology and genetic engineering have created enormous potential for marketing cellular by-products, including for example, proteins, including protein pharmaceuticals such as interferon, monoclonal antibodies, TPA (Tissue Plasminogen Activator), growth factors, insulin, and cells for transplantation. The demand for these products has grown tremendously and will continue to do so, creating a need for efficient methods of producing industrial quantities of cell-derived pharmaceuticals and other products. Further, the demand for efficient methods of analyzing and isolating biological products through chromatographic technology, and the need to improve bio-implantables continues to grow.

Research and study of cell structure and morphology are fundamental to continued progress in the diagnosis and treatment of human diseases. Numerous cell products are of vital importance therapeutically and commercially, including, for example, hormones, enzymes, viral products, vaccines, and nucleic acids. The production of these products requires large scale cell culture systems for their production.

Mammalian cells can be grown and maintained in vitro, but are generally anchorage-dependent, i.e., they require a solid surface or substrate for growth. The solid substrate is covered by or immersed in a nutrient medium particular to the cell type to be cultured. The nutrient medium and solid substrates are contained in a vessel and provided with an adequate supply of oxygen and carbon dioxide to support cell growth and maintenance. Cell cultures may be batch systems, in which nutrients are not replenished during cultivation although oxygen is added as required; fed batch systems, in which nutrient and oxygen are monitored and replenished as necessary; and perfusion systems, in which nutrient and waste products are monitored and controlled (Lubiniecki, *Large Scale Mammalian Cell Culture Technology*, Marcel Dekker, Inc., New York, 1990).

The primary commercial systems used for mammalian cell culture use solid matrix perfusion and microcarrier bead systems (Lubineicke, supra). The solid matrix perfusion systems utilize glass columns packed with glass beads or helices, which form a matrix as the solid substrate for cell growth. Once cells have attached to the matrix, medium is continuously recycled from a storage vessel for support of cell growth and maintenance. A similar perfusion system uses hollow fibers as the solid matrix instead of beads.

In microcarrier systems, small spheres are fabricated, for example, from an ion exchange gel, dextran, polystyrene, polyacrylamide, or collagen-based material. These materials have been selected for compatibility with cells, durability to agitation and specific gravities that will maintain suspension of the microcarriers in growth mediums. Microcarriers are generally kept in suspension in a growth medium by gently stirring them in a vessel. Microcarrier systems are currently regarded as the most suitable systems for large-scale cell culture because they have the highest surface to volume ratio and enable better monitoring and control. Nevertheless, current microcarrier culture systems have a number of serious disadvantages: small microcarrier cultures cannot be used to inoculate larger microcarrier cultures; therefore, a production facility must use other culture systems for this purpose; the cost of microcarriers is high, which can necessitate reprocessing of the microcarriers for reuse with the attendant costs; and the oxygen transfer characteristics of existing microcarrier systems are rather poor.

Specific forms of calcium phosphate ceramic have been identified for use in microcarriers to support anchorage-dependent cells in suspension. These specialized ceramics provide a material, which is biomimetic, i.e., it is composed of mineral species found in mammalian tissues, and which can be further applied to a variety of in vitro biological applications of commercial interest. A number of common cell lines used in industrial applications require attachment in order to propagate and need substrate materials such as microcarriers for large scale cultivation. U.S. Pat. No. 4,757,017 (Herman Cheung) describes the use of solid substrates of mitogenic calcium compounds, such as hydroxylapatite (HA) and tricalcium phosphate (TCP) for use in in vitro cell culture systems for anchorage-dependent mammalian cells. The unique features of this technology include the growth of cells in layers many cells thick, growth of cells that maintain their phenotype and the ability to culture cells for extended periods of time. Cheung demonstrated the application of this technology for culturing red blood cells. A current limitation of this technology is that the microcarriers are only available in a non-suspendable granular form. The density of these microcarriers further limits the ability to scale-up this technology for large bioreactors, which require a suspendable microbead carrier. Cheung, also describes the use of large substrates in monolithic forms for the culture of cells, but he does not identify methods for producing large area monoliths conforming to the contours and sizes of tissues to be replaced in vivo or grown in vitro. A complementary system using an aragonite ($CaCO_3$) is described in U.S. Pat. No. 5,480,827 (G. Guillemin et al). Although this patent also mentions the importance of calcium in a support system for mammalian cell culture, the calcium compound was not in a suspendable form. Likewise, Guillemin et al do not identify methods for producing large area monoliths conforming to the contours and sizes of tissues to be replaced in vivo or grown in vitro.

The concept of fabricating a suspendable microcarrier bead with a minor component of glass was discussed by A. Lubiniecki in *Large-Scale Mammalian Cell Culture Technology* in which a minimal glass coating was applied to a polymer bead substrate by a chemical vapor deposition process or low temperature process. This approach also was disclosed in U.S. Pat. No. 4,448,884 by T. Henderson (see also U.S. Pat. Nos. 4,564,532 and 4,661,407). However, this approach primarily used the polymer bead substrate to maintain suspendability.

An example of the use of non-suspendable or porous ceramic particles for cell culture is taught by U.S. Pat. No.

5,262,320 (G. Stephanopoulos) which describes a packed bed of ceramic particles around and through which oxygen and growth media are circulated to encourage growth of cells. U.S. Pat. No. 4,987,068 (W. Trosch et al.) also teaches the use of porous inorganic (glass) spheres in fixed bed or fluidized bed bioreactors. The pores of the particles act as sites for the culture of cells. Conversely, Richard Peindhl, in U.S. Pat. No. 5,538,887, describes a smooth surface cell culture apparatus which would limit cell attachment to chemical adhesion and prevent mechanical interlocking.

Macroporous glass beads also have been reported by D. Looby and J. Griffiths, "Immobilization of Cells In Porous Carrier Culture", *Trends in Biotechnology,* 8:204209, 1990, and magnesium aluminate porous systems by Park and Stephanopolous, "Packed Bed Reactor With Porous Ceramic Beads for Animal Cell Culture", *Biotechnology Bioengineering,* 41: 25-34, 1993. Fused alumina foams have been reported by Lee et al, "High Intensity Growth of Adherent Cells On a Porous Ceramic Matrix." *Production of biologicals from Animal Cells in Culture,* editors, R. E. Butterworth-Heinemann et al., pp. 400-405, 1991, and polyurethane foam by Matsushita et al., "High Density Culture of Anchorage Dependent Animal Cells by Polyurethane Foam Packed Bed Culture Systems", *Applied Microbiology Biotechnology,* 35:159-64, 1991.

Fluidized bed reactors have been used for cell culture as reported by J. M. Davis (editor), *Basic Cell Culture,* (Cartwright and Shah), Oxford University Press, New York, 1994, but require carrier systems with densities between 1.3 and 1.6 g/cc. According to Cartwright (J. M. Davis, supra.), generally, in fluidized beds, cells do not grow on the exterior surface of carriers where they would be dislodged by interparticle abrasion. Instead, as with macroporous microcarriers, they colonize the interior pores where they proliferate in a protected microenvironment. As examples, (Cartwright, supra, p. 78) cell carriers used in fluidized beds include glass beads (Siran by Schott Glass), and collagen microspheres produced by Verax. Cartwright also describes other conventional microcarriers weighted with TiO2 (Percell Biolytica products) and LAM-carrier polyethylene beads weighted with silica.

Hydroxylapatite and calcium phosphates have been used for implant applications with and without bone mixtures and bone growth factors. For example, Jarcho, *Dent. Clin. North Am.* 30:25-47 (1986) describes implanting of calcium phosphates to augment bone, while Ripamonti et al, *MRS Bulletin* 36-39 (November, 1996) describes augmentation of bone with bone morphogenic proteins (BMP's), including TGF-beta, BMP's 108, OP-1 and 2, and dimineralized bone matrix with and without hydroxylapatite. Other growth factors applicable for bone augmentation are also set forth by Lane et al, *Clinical Orthopaedics and Related Research,* 367S, S107-117 (October 1999), and include recombinant human bone morphogenetic protein (rhBMP), fibroblast growth factor (FGF), acidic fibroblast growth factor (aFGF), basic fibroblast growth factor (bFGF), insulinlike growth factor (IGF), platelet derived growth factor (PDGF), and growth differentiation growth factor (GDF). Various types of calcium implants, including tricalcium phosphate, hydroxylapatite, calcium phosphate and calcium carbonate, are listed in Han et al., *J. Western Soc. Periodontology:Perio Abstracts* 32(3):88-108 (1984). The use of dense and porous hydroxylapatite with and without grafted bone is reported in Matukas et al., *J. Neurosurgery,* 69:514-517 (1988). Similarly, Small et al., *Int'l J. of Oral Maxillofacial Implants,* 8(5):523-528 (1993) describes hydroxylapatite particles used with freeze dried bone to augment bone for implants.

Also, Hollinger, *United States Army Institute of Dental Research Information Bulletin,* 4(2) (Winter, 1990), lists grafting materials that include various commercial types of hydroxylapatite, tricalcium phosphates and bone grafts. Finally, several investigators have demonstrated the culturing of marrow tissues, stem cells, and periosteal-derived cells on calcium phosphate materials, which have subsequently been implanted in animal models to produce the formation of bone and/or cartilage tissue by osteochondrogenic induction. These investigators include Nakahara et al, *Clinical Orthopaedics,* (276):291-8 (March, 1992); Grundel et al, *Clinical Orthopaedics,* (266):244-58 (May 1991); Toquet et al, *Journal of Biomedical Research,* 44(1):98-108 (January 1999); Bruder et al, *Journal of Bone and Joint Surgery,* 80(7):985-96 (July 1998). However, none of these publications describe the use of hollow calcium-containing microspheres as implantable substrates. All of these approaches to the culture of anchorage dependent cells suffer from either the inability to grow cells in a suspendable environment or to allow an encapsulated volume in which cells can be grown or have a proven viability as an implant material. Furthermore, the mass of material implanted as a carrier of cellular components is generally in excess of what can be resorbed in a ready manner.

Bonding agents applied as coatings can be used in conjunction with hollow microspheres are sited in WO98/43558, and include both polymeric and calcium based cements. Resorbable polymers which are applicable for orthopedic augmentation applications have been summarized by Behravesh et al, *Clinical Orthopedics and Related Research,* 367S, S118-125 (October 1999), and include polylactic acid, polygalatic acid, polycaprolactone, poly α-hydroxy esters, polyphosphazenes, polyanhydrides, and polypropylene fumarate, U.S. Pat. No. 5,522,893 (Chow et al), sets forth a review of methods for making calcium phosphate cements, which can be employed for bone augmentation applications. Likewise, U.S. Pat. No. 4,612,053 (Brown et al) and U.S. Pat. No. 5,047,031 (Constantz et al) establish alternative and complementary methods of calcium phosphate cement formulation. Wright Medical Technology, Inc. (Memphis, Tenn.) has also produced a granular calcium phosphate for bone augmentation called Osteoset® and calcium sulfate used as a cement to incorporate a demineralized bone matrix called Allomatrix™ and further cites in its literature that calcium sulfate has been used for over 100 years as a bone void filler. Generally, cements used for bone augmentation applications lack sufficient porosity to allow for optimal bone in-growth and release of biological agents or live cells.

An excellent review of nitric oxide in biological applications is cited in the *Encyclopedia of Inorganic Chemistry,* Volume 5, 2482-2498, John Wiley & Sons (1994) and *Nitric Oxide in Health and Disease,* by J. Lincoln, Cambridge University Press, Cambridge, N.Y. & Melbourne, 1997. These references cite that nitric oxide (NO) is naturally produced in the body and is used on the cellular level as a defense against invading organisms, as a regulator of vascular tone and as a neuronal signaling agent. The concentration of nitric oxide and the presence of biological inhibiting agents or promoting agents determine the ultimate outcome, whether promoting tissue proliferation, health or tissue destruction.

According to these references, there are three types of cellular precursors to NO. They are all identified as nitric oxide synthases (NOS): Type I is associated with neurones, Type II is associated with a variety of cell types, but is primarily associated with host response to infection or invading organisms. Type III is primarily associated with endothelial cells.

NO has been implicated in increasing blood flow by arterial dilation, which can beneficially impact heart function, penile erection, and maintenance of blood supply to peripheral organs (Ziche et al, *Journal of Clinical Investigation*, 94, 2036-44. According to J. Lincoln, *Nitric Oxide in Health and Disease*, Cambridge University Press, Cambridge, N.Y. & Melbourne, 1997, NO and NO antagonist have been used to treat asthmatic conditions. Likewise, NO has been used to increase nerve function (Schuman et al, *Annual Reviews of Neuroscience*, 17, 153-83, 1994). Conversely, in larger concentrations, NO has been documented to be cytotoxic to tumor formations (Rocha et al, *International Journal of Cancer*, 63, 405-11, 1995), NO has also been suggested to play a number of roles in renal function including renal blood flow, renin secretion and pressure induced natriuresis and diaresis (Bachmann et al, *American Journal of Kidney Diseases*, 24, 112-29, 1994). NO has also been implicated as a growth factor (J. Lincoln, *Nitric Oxide in Health and Disease*, Cambridge University Press, Cambridge, N.Y. & Melbourne, 1997). Nitric oxide can also be used to treat pathogens and other invading organisms as set forth by James, S. L., *Microbiological Reviews*, 59, 533-47, 1995.

Tam et al, *Life Sciences*, 51, 1277-84, 1992 describes a method of producing NO from sodium nitrite and hydrochloric acid. NO can also be purchased as a purified gas from commercial suppliers such as Matheson Gas Products, Cucamonga, Calif. Also, Manahan in *Environmental Chemistry*, 6$^{th}$ Edition, Lewis Publishers (1994) describes methods for the formation of NO at high temperatures from $N_2$ and $O_2$ in controlled atmospheres. Ishii et al, *American Journal of Physiology*, 261, 598-603, 1991 describes a method of producing NO from sodium nitrite and hydrochloric acid.

The treatment of biological disorders with polymeric compounds binding NO compositions is set forth in U.S. Pat. No. 5,718,892 (Keefer et al). This patent further demonstrates the usefulness of delivering NO for other medical applications. Other precursor forms of NO compounds include nitric oxide synthase or L-arginine. Also, superoxide dismutase causes an increase in the production of free NO as cited by Hobbs et al, *Proceedings of the National Academy of Sciences USA*, November 8: 91, (23): 10992-6, 1994. Furthermore, NO is a physiological messenger and cytotoxic agent dependent on other mediating agents (J. Lincoln, *Nitric Oxide in Health and Disease*, Cambridge University Press, Cambridge, N.Y. & Melbourne, 1997).

NOS (nitric oxide synthases) Types I and III depend on elevated $Ca^{2+}$ levels to become activated, and Type II is regulated to a lesser degree by the presence of $Ca^{2+}$ (Jordan et al, *Surgery*, 118, 138-45, 1995). These references together indicate that all three types of nitric oxide synthases are regulated to some degree, either directly or indirectly, by the presence of calcium. Also, Schuman et al, *Annual Reviews of Neuroscience*, 17, 153-83, 1994 showed that phosphorylation of Type I NOS may form an additional mechanism for regulating its activity. Methods for extraction and purification of the three types of NOS are given by Fosterman et al, *Methods in Enzymology*, 233:258-64, 1994. It should also be noted that NOS is regulated by the presence of NO according to Rengasamy et al, *Molecular Pharmacology*, 1993, July, 44 (1): 124-8.

The current technology for the delivery of nitric oxide for medical applications generally relies on polymers for implant applications and does not anticipate the need for the presence of calcium and/or phosphate to regulate nitric oxide or nitric oxide precursors. Likewise, for non-implant applications nitric oxide components are generally delivered by inhalation, or as free pharmaceutical agents. Also, nitric oxide or substances containing nitric oxides, have not been previously encapsulated in or used in conjunction with ceramic or glass materials for the delivery of nitric oxide for medical applications.

Accordingly, a need exists for new implantable substrates as well as methods of effectively delivering NO to a desired site. The present invention satisfies this need and provides related advantages as well.

SUMMARY OF THE INVENTION

In one aspect of the invention, the disadvantages of the prior art are overcome by the present invention through the use of hollow calcium containing structures mixed with bone or bone derived substances. Thus, the hollow calcium containing structures function to supplement bone or bone derived substances and are, therefore, referred to as bone graft extenders.

Likewise, the same hollow calcium containing structures, with or without bone or bone derived materials, can be used in conjunction with bonding agents as materials for joining hollow microspheres or other hollow forms in a monolithic structure. Likewise, the bonding materials used to bond the hollow forms can also be used to bond to tissues at the implant site. These bonding agents can be either polymeric materials or calcium containing cements. Useful polymeric materials include, for example, polylactic acid, polyglycolic acid, polycaprolactone, poly α-hydroxy esters, polyphosphazenes, polyanhydrides, and polypropylene fumarate. The calcium in the cements is preferably calcium phosphate, calcium sulfate or a mixture thereof. The desired amount of calcium containing cement ranges from about 5% to about 75%, and more preferably from about 10% to about 50% by volume of the total composition.

Furthermore, this invention sets forth a method for encapsulating nitric oxide gas or nitric oxide containing compounds, or precursors to nitric oxide (also referred to herein as "nitric oxide forming compounds") in conjunction with calcium containing materials for medical therapeutic applications. This invention also provides methods for coating surfaces of calcium containing compounds or mixing calcium containing compounds with precursors of nitric oxide, and/or antagonists or activators to nitric oxide formation.

Also described in this invention is a method for fabricating calcium containing substrates with surfaces, which conform to tissue surfaces in the body requiring replacement or augmentation. These substrates are fabricated from the cast tape process to produce sheet structures, which are flexible in the unfired state, and can be contoured by firing on refractory shapes, which conform to the site of implantation. Furthermore, the invention comprises a method for using the cast tape components and building them up in layers to produce the desired shape as substrates for cell culturing applications. The cast tape components are built up in the same manner as three dimensional topographic structures. In each case these substrates can be implanted with or without the cultured tissue to augment the desired implant site.

DETAILED DESCRIPTION OF THE INVENTION

The invention relates to the use of hollow calcium-containing microspheres for a variety of purposes. Such uses include bone graft extenders, bonding agents, cell culture substrates and carriers of nitric oxide.

A. Bone Graft Extender

In one aspect, the invention relates to methods of making a bone grafting mixture in which the calcium-containing microspheres or other hollow microstructures are used to extend bone material. The methods are generally accomplished by:

(a) obtaining hollow calcium-containing microstructures; and (b) mixing the hollow calcium-containing microstructures with a bone material to form a bone grafting mixture.

Useful hollow calcium-containing microstructures for these methods include the hollow calcium phosphate (CaP) microspheres as described in PCT publication WO 98/43558, incorporated herein by reference. Particularly useful calcium phosphate for making the hollow CaP microstructures includes hydroxylapatite, tricalcium phosphate (alpha- and/or beta-), dicalcium phosphate (hydrous and/or anhydrous forms), and tetracalcium phosphate. These hollow microstructures can be fabricated in porous or dense form as described in PCT publication WO 98/43558.

Alternatively, hollow calcium oxide/calcium hydroxide microstructures or mixtures of hollow CaP and calcium oxide/calcium hydroxide microstructures can be used. These can be prepared in the same manner as described for calcium phosphate microspheres in PCT publication WO 98/43558 or as described in U.S. Pat. No. 4,133,854, incorporated herein by reference, which describes methods for making small hollow glass, metal or plastic microspheres.

The hollow calcium-containing microstructures are mixed with a mixture containing bone (referred to herein as "bone mixture" or "bone material"). The bone mixture can be comprised of cancellous bone and/or de-mineralized bone matrix (DBM), which is made from tissue bank processed freeze drying methods as described, for example, in Friedlaender et al., *Osteochondral Allografts*, pp 181-192 (Little, Brown & Co., Boston/Toronto 1983). The bone mixture and hollow microspheres are either dry mixed in a container with a spatula or other mixing tool or device. The components can be mixed in saline, distilled water, blood, other physiologically-acceptable fluid or a mixture thereof. In addition, bone growth factors can be mixed with this mixture. Useful bone growth factors are listed in Repamonti et al., *MRS Bulletin*, 36-39 (November, 1996).

The volume amount of bone material in the bone grafting mixture can range from about 5% to about 95% or more typically from about 50% to 75%. The amount of bone mixture depends on the extent of ingrowth of bone desired within the hollow microspheres and, if desired, the subsequent resorbtion of the hollow microspheres. Both the extent of bone in-growth and resorbtion of the microspheres can be controlled by adjusting the calcium content and porosity of the hollow microspheres, which can be readily determined by those skilled in the art and from the teachings of PCT publication WO 98/43558.

The present invention further provides methods for using the bone grafting mixture in which the mixture is implanted in bone defects or in surgical sites where bone growth or augmentation is desired. Those skilled in the art can readily determine the amount of bone grafting mixture to be implanted depending on several factors including, for example, the extent and location of bone defect or surgical site to be augmented. The advantages of the present methods over known mixtures of bone material and non-hollow particles is that bone growth can also occur within the hollow microstructures rather than around the non-hollow particles, thus providing a better matrix for bone growth. Also, the hollow structure of the calcium material provides an optimal structure for maximizing bone in-growth and eventual replacement of the calcium containing material, while maintaining mechanical integrity of the implanted mixture. In any event, the hollow structure provides a lower mass of calcium containing material to be replaced at the implant site by host tissues. In addition, the hollow microspheres can undergo subsequent resorbtion by adjusting the calcium content and porosity of the microspheres depending on the desired rate of resorbtion.

B. Bonding Agent

Another aspect of the invention relates to calcium-containing bonding agents that can be used to produce the calcium-containing microstructures or for inclusion in the bone grafting mixture described above. Particularly useful bonding agents include various calcium cements containing, for example, calcium phosphate, calcium sulfate, calcium oxide/calcium hydroxide or a mixture of CaP and calcium oxide/calcium hydroxide.

Typically, the cement is comprised of an anhydrous or semi-anhydrous form of the calcium component, for example, an anhydrous or semi-anhydrous form of calcium phosphate or calcium sulfate. Preferably, the cement component of the cement/bone grafting mixture ranges from about 5 to about 75 volume percent, and more preferably from about 10 to 50 percent by volume, for the total mixture. One skilled in the art can readily determine the desired percentage depending on, for example, the intended use and if resorbtion is desired.

An example of a calcium containing cement is described in U.S. Pat. No. 5,522,893 (Chow), incorporated herein by reference. The calcium phosphate cement is prepared by mixing tetracalcium phosphate and dicalcium phosphate anhydrous at a molar ratio of 1:1, and mixing with 25 mmol/L phosphoric acid at a powder to liquid ratio to 4.0 at ambient temperature. This mixture is subsequently stirred into the hollow microspheres at 50 percent by volume. The mixture is delivered to the implant site and allowed to set by hydrothermal curing. A similar example of bonding the hollow microspheres would be the replacement of the calcium phosphate cement with a mixture of plaster-of-Paris (hemi-hydrate salt of calcium sulfate) in an aqueous or acidic media, such as distilled water for example.

Also, the bonding agent can be a mixture of polymeric material and hollow calcium containing microstructures. Useful polymeric materials include polylactic acid, polyglycolic acid, polycaprolactone, poly α-hydroxy esters, polyphosphazenes, polyanhydrides, and polypropylene fumarate. A specific example of a bonding agent is based on mixing crosslinkable polyanhydride polymers by photo polymerization as described by Muggli, D. S. et al., *Macromolecules*, 31, 4120-25, (1998). In this example, 10 percent by volume of said polyanhydride polymer is mixed with 90 percent by volume of hollow microspheres. The mixture is delivered to the implant site and cured in situ using a photo polymerizable light source.

Hollow calcium phosphate microspheres can also be fabricated from calcium cements, which have the advantage of being able to bond to each other by the addition of aqueous media. For example, these can be prepared in the same manner as described for calcium phosphate microspheres in PCT publication WO 98/43558 with the exception of using tetracalcium phosphate and dicalcium phosphate anhydrous materials as starting materials in a molar ratio of 1:1 in place of hydroxylapatite or tricalcium phosphate. (See U.S. Pat. No. 5,522,893 (Chow)). These materials must be applied to wax or other organic microspheres in powder form or other non-aqueous form (solvent based, such as methyl ethyl ketone or terpene, for example) form to prevent hydration of the starting powders. The resulting coated spheres must be heated to decompose the organic components, and, in the case of a solvent processed material, to remove the solvent. The resulting spheres can be bonded by mixing with 25 mmol/L phosphoric acid in a sphere to liquid ratio of 4.0 at ambient temperature.

The benefit of adding a bonding agent to the above mixtures is that they gain mechanical integrity and can better conform to the site of implantation. Likewise, they can bond with the tissue at the implant site. Also, by adjusting the amount of bonding agent, a high degree of open porosity can be maintained, which enhances bone in-growth.

C. Nitric Oxide Carriers

A further aspect of the present invention relates to the beneficial effects of nitric oxide for enhancing tissue growth and proliferation. More particularly, the invention relates to the (1) containment of NO gas or (2) liquid containing NO in concentrations of the desired amount or (3) precursor compounds to NO all of which are intended to provide a therapeutic effect or enhance proliferation of cells or tissues during cell culturing through action as a growth factor. Such concentration can be controlled by dilution of the entrained NO with inert gases such as argon. Likewise the concentration of NO in the liquid can be controlled by similar methods.

The primary reason for using a calcium substrate is that NOS Types I & II depend on elevated $Ca^{2+}$ levels to become activated. Likewise, Type III also is regulated to a lesser degree by the presence of $Ca^{2+}$. For this reason, implantable substrates, including for example calcium phosphates, calcium oxide, and Bioglass™ (calcium phosphate glasses) are useful candidates for the delivery of NOS to the site of implantation or during cell culturing. Likewise, these calcium-containing substrates are useful candidates for the delivery of cell types that produce the required NOS type at the implant site. Furthermore, agents such as L-arginine and aminoguanidine can also be delivered as agents which mediate the formation of NO within the cells. However, the mechanism for producing the desired response is also dependent on the resulting concentration of NO and the presence or absence of other known activators and inhibitors. These precursors, inhibitors and activators can be delivered simultaneously or in subsequent deliveries to the implant site or cell culture media.

Accordingly, the present invention relates to novel methods for delivering nitric oxide to localized sites, for example, implant sites or bioreactors for the case of cell culture. The methods are generally accomplished by initially encapsulating nitric oxide or precursor to NO within or on a calcium phosphate or other biocompatible material, including, for example, the porous or hollow microstructures described above or calcium-containing particulates.

For example, NO gas or liquids containing NO can be encapsulated in hollow portions of calcium/phosphate glass and placed or injected into the implant site, and the encapsulated nitric oxide is subsequently released in vivo or in vitro by resorbing the implantable material for therapeutic purpose. Likewise, the NO gas or gas containing liquid could be infiltrated into porous or hollow calcium/calcium phosphate particles which are subsequently sealed with a bioresorbable polymer such as polylactic acid, polyglycolic acid, polycaprolactone, poly α-hydroxy esters, polyphosphazenes, polyanhydrides, and polypropylene fumarate or other biocompatible, bioresorbable and/or biopermeable polymer. Subsequent to implantation the polymer would either resorb or allow for the release of the NO. The gas can be incorporated in the glass fiber, bead or other hollow form by having a saturated atmosphere of the gas, in which the a molten form is enclosed around the gas, or the hollow form openings are pinched shut by melting the glass. In a manner similar to ampoules, which contain liquid solutions of ammonia in small, sealed glass containers, liquids containing NO can be prepared for implant site delivery. Liquids such as water containing NO could be used to saturate porous or hollow structures which are subsequently sealed in place by organic or polymer coatings as previously cited, or by entrapment by localized melting of hollow structures openings such that they are closed off by the hosting material.

Biological glasses (e.g., Bioglass®) can be used for implant applications. Biological glasses are sodium silicate based but incorporate CaO and $P_2O_5$ in their composition. Typical compositions are described in U.S. Pat. No. 5,981,412 (Hench et al) and U.S. Pat. No. 4,608,350 (Howard), incorporated herein by reference. The properties of molten glass are conducive to hollow shape fabrication techniques (such as light bulbs) known to those skilled in the art are described in *The Technology of Glass and Ceramic: An Introduction, Glass Science Technology*, No. 4, J. Hlavac, Elsevier Scientific Publishing Co., N.Y. & Amsterdam (1983), incorporated herein by reference. Methods for making glass microspheres are detailed in U.S. Pat. No. 5,176,732 (Block et al), U.S. Pat. No. 4,133,854 (Hendricks), and U.S. Pat. No. 4,767,726 (Marshall), all incorporated herein by reference. Furthermore, methods for introducing a gas into glass microspheres are given in U.S. Pat. No. 4,257,798 (Hendricks et al) and U.S. Pat. No. 4,547,233 (Delzant), both incorporated herein by reference.

Other methods for making gas-containing structures for gases other than NO are readily known to those skilled in the art, including, for example, the methods described in U.S. Pat. No. 4,257,798, incorporated herein by reference, which describes methods for introducing gases into microspheres. Alternatively, the calcium and/or calcium phosphate material could also be encapsulated in a particulate form in a carrier polymer, thereby gaining the activating nature of the $Ca^{2+}$ released from the calcium containing compound.

The delivery of NO or other NO inducing agents or cells also has application in the in vitro culture of cells (cell culture/bioreactor applications) and tissues and bio-products derived from them. Examples of calcium containing structures with some form of NO are provided in the Examples below.

All of the compositions described in the examples can be used as medical therapeutic agents or enhancements for cell culture applications.

D. Substrate for Cultured Cells

The present invention further relates to methods of culturing cells on calcium-containing substrates, conforming to tissue to be replaced in vivo. A variety of calcium compounds can be used as cell culture substrates, including, for example, calcium oxide, Bioglass, dicalcium phosphate, tricalcium phosphate, hydroxylapatite, tetracalcium phosphate, and the like.

The substrates can be in any desired geometrical form or shape, including, for example, microspheres, planar, tubular, three dimensional scaffold, or other geometrical form that complements the missing tissue at the site to be constructed. The microspheres can be produced, for example, as described in WO 98/43558, while the other geometrical shapes can be fabricated by any method known to those skilled in the art, including customary ceramic powder fabrication methods, such as, for example, tape casting, slip casting, gel casting, extrusion, isostatic pressing, tape lamination and molding processes such as injection or transfer molding. After the forming step, the substrate in the desired geometric shape is sintered to the desired porosity, density and strength state. For example, the substrates can be produced by ceramic processing methods in which various densities can be obtained through firing as described in Reed, *Principles of Ceramic Processing*, 2d ed. (John Wiley & Sons, NY, 1995).

Methods for fabricating cast tape ceramic components from oxide materials are well known to those skilled in the art of ceramic component fabrication, and is described for example in Reed, *Principles of Ceramic Processing*, second edition, pp 525-540 (John Wiley & Sons, NY, 1995), incorporated herein by reference. For example, thin, flexible green sheets of CaP compositions can be produced with either a batch or continuous cast tape process. Relevant CaP compositions are, comprised of hydroxylapatite, tribasic calcium phosphate, dicalcium phosphate (hydrous or anhydrous), calcium carbonate, calcium oxide, Bioglass or any mixture thereof. The initial step for cast tape processing requires a concentrated, milled ceramic slurry containing dispersed CaP powders mixed with a relatively high concentration of polymeric binders and plasticizers in a solvent medium system. A thin, flexible CaP tape is formed when the ceramic slurry flows beneath a blade (known as a doctor blade in the industry) forming a film on a moving carrier of a high surface quality polymeric carrier such as a polyester film (Mylar®), which is then dried in a controlled temperature environment.

In a batch process, thin sheets of CaP ceramic can be formed by pouring the ceramic slurry into a doctor blade mounted in a box assembly and moving the blade assembly over a stationery carrier film such as Mylar® supported by a flat ground surface plate made of glass or metal. In the batch process, the cast tape is then allowed to dry to remove the solvent medium. The resulting dried cast tape is flexible with a smooth surface texture, which allows for green ceramic sheets to be separated from the polymeric carrier film, which are then cut to size. In a continuous process, the doctor blade box assembly is held in a fixed position and the carrier film is continuously run underneath the doctor blade for depositing a thin film of ceramic slurry. The ceramic slurry is then dried in a controlled heated atmosphere prior to stripping of the ceramic cast tape. For both processes, the green-state CaP tape can be handled as separate sheets or can be rolled for storage prior to cutting into sized shapes.

With the high concentration of polymeric binders and plasticizers in the green-state ceramic tape, individual sized shapes may be sintered to form flat, thin substrates. Also, individual layers of tape can be formed over contoured surfaces by subsequently heating the cast tape to thermoplastically deform the cast tape followed by cooling to establish the contoured shape. This process is possible as a result of the flexible, rubbery nature cast CaP tape layers that adapt to the shape of specific forms to be replicated. After the contouring process to establish shape, a low temperature treatment of approximately 300° C. is used to partially decompose the binder and to rigidize the CaP sheet structure. If needed, this process may benefit from a refractory support structure during thermal curing of the ceramic tape, which can be fabricated from plaster-of-Paris or a commercial castable cement. A castable refractory material may also be employed to support the contoured CaP cast tape shape during the high temperature sintering process, which occurs over the temperature range from approximately 1100° C. to 1400° C.

Also, individual layers of green-state CaP cast tape may be laminated to bond individual sheets in forming a monolithic structure which is then sintered. Three dimensional structures can then be fabricated starting with individual sheets of cast tape. Using a computer generated model, three dimensional structures can be sectioned into separate thin layers by computer simulation. These dissected thin layers are then fabricated from cast tape sheets. The exact outline configuration of each cast tape sheet is defined by a laser generated contour using computer-aided design methods established in the industry. Each cast tape outline is created using automated control of a laser beam to precisely cut each layer of tape representing a dissected section of the actual model to be recreated in an appropriate calcium containing composition. The individual layers of tape are then assembled and laminated with aid of heat and pressure (with or without solvent) to form an actual replica of a three-dimensional contoured shape. By characterizing the shrinkage of the cast tape during sintering, the size of each cast tape shape in the assembled unit is adjusted to compensate for shrinkage.

The primary steps that comprise the basic cast tape process for preparing thin sheets to be used as substrates for flat geometries, contoured surfaces or laminated three-dimensional structures are comprised of the following:

Ball milling of CaP powder, binder(s), plasticizer(s), deflocculant (dispersant) and solvent(s).
Mixing step
De-airing
Filtering
Tape casting
Drying
Separation of cast tape from carrier film
Cutting shapes from cast tape sheets to size The specific CaP composition can be tailored for exacting properties defined by chemistry and processing conditions, which as an example, defines its ability to resorb in cell culturing either in vitro or in vivo for implant applications.

The cast tape process can be successfully accomplished using several types of binder systems, depending on whether an aqueous or non-aqueous solvent system is employed. A typical solvent system is comprised of ethyl or methyl alcohol blended with methyl ethyl ketone or toluene. For this solvent system, a common binder used in ceramic tape formulations is polyvinyl butyral (Butvar® PVB B72 or B90) and a phthalate plasticizer (Santicizer® 160). An acrylic (Acryloid® B-7 in methyl ethyl ketone solvent) has been shown to be an alternative to PVB for improved binder burn-out with little or no measurable ash content. As a dispersant in solvent systems, Menhaden fish oil has been shown to work well in deflocculating the CaP particles and to improve release of cast tape from the polymer film carrier.

The use of aqueous based acrylic emulsions provides an alternative and effective processing path for minimizing the health effects and hazards of organic solvents such as toluene and methyl ethyl ketone. One system that has been identified is based on Rohm & Haas' Duramax family of acrylic emulsions. The ability to obtain a high solids loading of CaP powder in water begins with the use of acrylic dispersants such as Duramax D-3005 or D-3021 or R. T. Vanderbilts' well know Darvan family of dispersants such as Darvan C or Darvan 7. One example of an acrylic cast tape system is comprised of:

100 grams of calcium phosphate processed powder (HA/TCP mixture)
55 grams of de-ionized water
0.86 grams of Duramax D-3021
Ball mill for 2-3 hours, then mix by agitation at 100-300 rpm:
12.7 grams of Duramax B-1001 ceramic binder (55% solids, 7% solids basis)
3.0 grams of Polyethylene Glycol 300 MW (Polysciences)
De-airing step followed by tape casting.

Other acrylic emulsion resins can be blended with or substituted for Duramax B-1001 to adjust the $T_g$ (glass transition temperature); thereby, increasing or decreasing the flexibility of CaP cast tape. Such alternative resins include Duramax B-1080 to include the flexibility of CaP cast tape. Duramax B-1080 is also an effective binder for producing ultra-thin cast tapes having a thickness less than 50 micrometers. Other acrylic resins known in the art for casting ceramic tapes include Duramax B-1080 and B-1000.

Alternatively, the substrate of the present invention can be produced by melting a glass composition containing calcium phosphate and fabricating the desired structure using well established glass forming methods based on melt processing techniques known to those skilled in the art, including for example, the methods described in *The Technology of Glass and Ceramic: An Introduction, Glass Science Technology No. 4*. Hlavac. Elsevier Scientific Publishing Co. 1983. NY, Amsterdam.

Methods for using the cells and tissues cultured on the calcium-containing substrates are also within the present invention. In these methods, the desired geometric shape of the cultured cells/tissues depends on the tissue to be replaced, repaired or augmented in the patient. More specifically, the tissue that is replaced, repaired or augmented can include bone, cartilage, tendon, ligament, skin, muscle, kidney, heart, pancreas, or cardiovascular, neural, urological, respiratory, intestinal, endocrine and liver tissues. For example, tubular structures can be used for veins, arteries, or other forms to conform to the implant sites such as cartilage and ligaments.

The cells or tissues are grown on the calcium-containing substrates according to cell culture conditions known to those skilled in the art or as described in Example 6 below. Once a desired amount of cell growth has occurred, the cultured cells/tissues that have the desired geometric shape can be physically or chemically removed from the calcium-containing substrate and transplanted to the defect or surgical site to be augmented according to procedures known to those skilled in the art. Alternatively, the cultured cells/tissues can be transplanted with the calcium-containing substrate to the defect or surgical site to be augmented. Methods of transplanting are known in the art, including, for example, those methods described in *Synthetic Biodegradable Polymer Scaffolds* by Anthony Atala et al, Editors, (Birkhauser Publishing, Boston 1997) and *Frontiers in Tissue Engineering*, Charles W. Patrick Jr. et al, Editors (Elsevier Science Ltd. 1998), both incorporated herein by reference.

The following examples illustrate, but are not intended to limit, various embodiments of the present invention.

EXAMPLE 1

NO Gas Containing Structures

NO gas obtained from Matheson Specialty Gas or NO produced from methods as previously described above is introduced into an evacuated chamber and is backfilled while forming hollow glass microspheres as described in U.S. Pat. No. 4,257,798 (Hendricks et al). In this example, hollow glass microspheres are fabricated in a glass composition according to U.S. Pat. No. 5,981,412 (Hench et al), which is approximately 47% $SiO_2$, 24% CaO, 24% $Na_2O$ and 5% $P_2O_5$. The glass composition is initially melted above 800° C. and processed according to Hendricks to produce NO containing hollow microspheres. This method may be improved upon by making NO gas in situ by introducing nitrogen and oxygen gases at temperatures greater than 800° C. to form NO during the glass hollow structure fabrication.

EXAMPLE 2

NO Gas Containing Structures

NO gas obtained from Matheson Specialty Gas or NO produced from methods as previously described is introduced into an evacuated glass tube or hollow fiber. After filling with NO gas, the glass tube or hollow fiber is cut with a Nichrome wire, which is resistance heated above 800° C. and is rapidly passed through the glass structure to seal the NO gas within the segmented structures without decomposition of the encapsulated NO gas. This technique can also be used to encapsulate NO aqueous containing solutions by introducing the liquid into the glass tubes or hollow fibers.

EXAMPLE 3

NO Gas Containing Structures Sealed with Polymer

A porous calcium containing structure such as a mixture of 75% by weight of tricalcium phosphate and 25% by weight of hydroxylapatite is synthesized into 500 micron diameter hollow microspheres or particles. The structure is then sintered above 1000° C. to produce porous structures. These microspheres or particles are subsequently placed in an evacuated chamber and backfilled with NO gas as previously described and at one atmosphere pressure in a sealed, heated vessel having a stirrer. The vessel containing the NO treated microspheres or particles is heated above the melting point of the polymer. The melted polymer such as polycaprolactone is then titrated into the sealed vessel as the microspheres or particles are stirred. A sufficient amount of polymer is titrated onto the hollow microspheres or particulates to the extent that agglomeration of the particles is initiated. The amount of polymer can be adjusted to change the rate of biodegradation. Stirring is continued while the polymer coated agglomerates are allowed to cool to form a sealed surface on the agglomerated microspheres or particulates. Also, solution polymerization in a controlled NO atmosphere can be used instead of melting a polymer for producing a polymeric coating encapsulating NO with hollow microspheres or particulates.

EXAMPLE 4

NOS or NO Precursor Coatings on Calcium Containing Hollow Microstructures or Particulates A porous calcium containing structure such as a mixture of 75% by weight of tricalcium phosphate and 25% by weight of hydroxylapatite is synthesized into 500 micron diameter hollow microspheres or particles. NOS is prepared by methods set forth by Fosterman et al, *Methods in Enzy-*

*mology*, 233, 258-64, 1994. The desired NOS type, such as Type I, is mixed with the calcium containing hollow microstructures or particulates to form a coating upon same. Likewise, L-arginine can be used as an NO precursor or with superoxide dimutase as an enhancer of biological activity and mixed the calcium containing hollow microstructures or particulates to form a coating upon same as described above. A further modification to Type II NOS is the incorporation of NO inhibitors such as aminoguanidine to regulate the release of NO as specified in *Nitric Oxide in Health and Disease*, by J. Lincoln, Cambridge University Press, Cambridge, N.Y. & Melbourne, p. 153, 1997.

EXAMPLE 5

Polymeric Materials, which Release NO Used in Conjunction with Calcium Containing Compounds A calcium containing structure such as a mixture of 75% by weight of tricalcium phosphate and 25% by weight of hydroxylapatite is synthesized into 500 micron diameter hollow microspheres or particles. The said structure is mixed with a polymeric material, which releases NO as described by U.S. Pat. No. 5,994,444 (Trescony et al). For instance, a polylactic acid and polyglycolic acid copolymer with inorganic nitrite dispersed within the copolymer is then mixed with greater than 5 percent by volume of the said calcium containing structure. Said mixture can be used with or without NOS additions.

EXAMPLE 6

Culture of Osteoblasts on Calcium Phosphate Microcarriers

The human fetal osteoblast cell line hFOB 1.19 was obtained from the American Type Culture Collection (ATCC, catalog no. CRL-11372). The cells are attachment dependent and are propagated in the growth medium specified by ATCC: a 1:1 mixture of Ham's F12 medium (Gibco catalog no. 21700, powder) and Dulbecco's modified Eagle's medium (Gibco catalog no, 13000, powder) with 2.5 mM L-glutamine and supplemented with 2.44 g/liter sodium bicarbonate, 0.3 g/liter neomycin G418, and 10% fetal bovine serum. These cells have been transfected with a reporter gene for the expression of the enzyme alkaline phosphatase, hence G418 is needed for selection pressure. As explained in the Product Information Sheet from ATCC, when these cells are grown at the permissive temperature of 34° C., they exhibit rapid cell division. However, little or no cell division occurs at a restrictive temperature of 39.5° C., rather, the cells differentiate and a more mature osteoblast phenotype is produced. Because undifferentiated, rapid cell growth was wanted, these osteoblasts were grown in an incubator at 34° C. in an atmosphere of 5% CO2. ATCC reports a doubling time of 36 hours for these cells at 33.5° C.

Upon thawing, the cells were transferred to a 15 ml centrifuge tube containing 10 ml of complete medium, centrifuged at ~800 rpm for 3 minutes, resuspended in 8 ml of complete medium, and transferred to 75 cm$^2$ tissue culture flask. Osteoblasts were subcultured upon reaching confluence in the flask by removing the culture medium from the flask, washing the cells once with PBS (phosphate buffered saline) containing 0.2 g/liter EDTA34Na (ethylene diamine tetracetic acid), then detaching the cells by incubating them in the presence of 0.25% trypsin-EDTA for 4 minutes at 34° C. The trypsin was inactivated by the addition of complete medium and the osteoblasts were diluted 1:5 with fresh medium in a new flask.

The experiment to assess growth of the osteoblasts on the calcium phosphate microspheres was done in a 250 ml spinner flask, which had been siliconized to inhibit the attachment of cells to the glass walls of the spinner flask. A volume of 20 ml of calcium phosphate hollow microspheres (specific gravity of 1.05 grams/cc—2 mm diameter—H$_2$O impervious surface) was placed in the spinner flask with about 30 ml of cell culture grade water and sterilized by autoclaving for 30 minutes. After the flask cooled, the water was removed and the calcium phosphate microspheres were washed twice with 25 ml of complete medium. Inoculum for the experiment was grown in a 162 cm$^2$ tissue culture flask. When the osteoblasts reached confluence, the cells were detached by trypsinization, diluted in 39 ml of complete growth medium and transferred to the sterile spinner flask. A sample of the inoculum was used for counting the cells to determine the seed concentration. It was determined that $1.076 \times 10^7$ cells were added to the spinner. The spinner was placed in the incubator without agitation to allow the cells to attach. After about 12 hours, the agitation was started at 20 rpm in order to provide better oxygen transfer into the medium. Glucose and lactic acid were assayed daily as an indirect measurement of cell growth. The growth medium was replaced every four days or whenever the glucose concentration fell below 1.5 g/liter. Multiple layers of cells were demonstrated to grow under these conditions as shown by scanning electron microscope micrographs.

While various embodiments of the present invention have been described in detail, it is apparent that modifications and adaptations of those embodiments will occur to those skilled in the art. It is to be expressly understood, however, that such modifications and adaptations are within the scope of the present invention.

The invention claimed is:

1. A method of making a calcium-containing substrate, comprising the steps of:
    (a) obtaining a composition comprising calcium phosphate-containing hollow microspheres having a diameter between about 0.5 mm and about 6 mm;
    (b) forming a three-dimensional shape from the calcium phosphate-containing hollow microspheres by CAD-CAM processing, wherein the three-dimensional shape conforms to tissue to be replaced or augmented in a patient; and
    (c) culturing cells or tissues onto the three-dimensional shape to form the calcium-containing substrate.

2. The method of claim 1, wherein calcium phosphate is hydroxyapatite, tribasic calcium phosphate, dicalcium phosphate, tetracalcium phosphate, calcium carbonate, calcium oxide, glass-containing calcium phosphate, or a mixture thereof.

3. The method of claim 1, wherein said three-dimensional shape is fired prior to step (c).

4. The method of claim 1, wherein the cells or tissues can be cultured on both sides of the three-dimensional shape.

5. The method of claim 4, wherein one cell or tissue type is cultured on one side of the three-dimensional shape and a second cell or tissue type is cultured on a second side of the three-dimensional shape.

6. A method of treatment of a patient in need of an implant, comprising transplanting a calcium-containing substrate in the patient, wherein the calcium-containing substrate is produced by a process comprising:

(a) obtaining a composition comprising calcium phosphate-containing hollow microspheres having a diameter between about 0.5 mm and about 6 mm;
(b) forming a three-dimensional shape from the calcium phosphate-containing hollow microspheres by CAD-CAM processing, wherein the three-dimensional shape conforms to tissue to be replaced or augmented in a patient; and
(c) culturing cells or tissues onto the three-dimensional shape to form the calcium-containing substrate.

* * * * *